(12) United States Patent
Sramek et al.

(10) Patent No.: US 6,767,740 B2
(45) Date of Patent: Jul. 27, 2004

(54) STEM CELL AND DENTAL PULP HARVESTING METHOD AND APPARATUS

(76) Inventors: Roger Anton Sramek, 88 Prospect Ave., Sausalito, CA (US) 94965; Bahram Javid, 8359 Kent Dr., El Cerrito, CA (US) 94530

( * ) Notice: Subject to any disclaimer, the term of this patent is extended or adjusted under 35 U.S.C. 154(b) by 0 days.

(21) Appl. No.: 09/975,041

(22) Filed: Oct. 9, 2001

(65) Prior Publication Data

US 2003/0068305 A1 Apr. 10, 2003

(51) Int. Cl.[7] .............................. C12N 5/00; C12N 1/00
(52) U.S. Cl. ...................... 435/378; 435/325; 435/373; 435/317.1
(58) Field of Search ................................. 435/378, 325, 435/373, 317.1

(56) References Cited

U.S. PATENT DOCUMENTS

| | | | |
|---|---|---|---|
| 5,913,859 A | 6/1999 | Shapira | 606/80 |
| 6,110,176 A | 8/2000 | Shapira | 606/80 |

OTHER PUBLICATIONS

Pissiotis et al. Dentin as inhibitor of bacterial toxicity cells on pulpal cells in vitro. J Endod. Apr 1992;18(4):166–71.*

Moule et al. Donor variability in the proliferation of human dental pulp fibroblasts. Aust Dent J. Apr 1995;40(2):110–4.*

Nakashima. Establishment of primary cultures of pulp cells from bovine permanent incisor. Arch Oral Biol. 1991;36(9):655–63.*

Duffy et al. Isolation of tooth pulp cells for sex chromatin studies in experimental dehydrated and cremated remains. Forensic Sci Int. Mar 1991;49(2):127–41.*

Shi et al. Perivascular niche of postnatal mesenchymal stem cells in human bone marrow and dental pulp. J Bone Miner Res. Apr 2003;18(4):696–704.*

Krebsbach et al. Dental and skeletal stem cells: potential cellular therapeutics for craniofacial regeneration.J Dent Educ. Jun 2002;66(6):766–73.*

Gronthos et al. Postnatal human dental pulp stem cells (DPSCs) in vitro and in vivo. Proc Natl Acad Sci U S A. Dec. 5, 2000;97(25):13625–30.*

U.S. patent application Ser. No. 60/310,304, Sramek.

The National Institutes of Health, "Stem Cells: Scientific Progress and Future Research Directions," p. ES 1–10, 1–3, 11–21, 23–42, 43–58 (Jun. 2001).

\* cited by examiner

*Primary Examiner*—David Guzo
*Assistant Examiner*—Daniel M. Sullivan
(74) *Attorney, Agent, or Firm*—Thomas W. Cook (57) ABSTRACT

Methods and apparatus for recovering dental pulp from dentition of a donor are disclosed, wherein the pulp from within extracted teeth utilizing such methods and apparatus is harvested, while preserving a sterile environment and avoiding trauma and infection, and stem cells, dendritic cells, and other cells isolating from the pulp, and the various cells propagated and expanded for subsequent use in repair or regeneration of tissues of the body, for therapeutic treatments, and other medical purposes.

2 Claims, 6 Drawing Sheets

STEM CELL AND DENTAL PULP HARVESTING METHOD AND APPARATUS

TECHNICAL FIELD OF THE INVENTION

The present invention relates generally to methods and apparatus for recovering dental pulp from dentition of a patient or other donor, in order to use the pulp so secured, and the stem cells and other cells contained in the pulp, for beneficial medical purposes. More specifically, the present invention relates to a method of obtaining dental pulp from teeth at times and under conditions most suitable, such as during normal tooth loss of "deciduous" teeth. At such times teeth may be taken, and the pulp from within the teeth extracted or "harvested," while preserving a sterile environment to avoid contamination of the pulp and, at the same time, avoiding trauma and infection of the donor. The pulp so secured may be utilized by isolating from it "stem cells," which may exhibit an ability to differentiate into cells of the same or other types, or propagated and manipulated to exhibit such "plasticity," for subsequent use in repair or regeneration of the same or other tissues of the body. The pulp may also be utilized by isolating from it other kinds of cells, such as dendritic cells which may exhibit an ability to detect hostile proteins foreign to a patient's body, for subsequent use in therapeutic treatments.

BACKGROUND ART OF THE INVENTION

In recent years, scientific interest has increased in cell biology in the areas of the derivation of cells, and the ability of certain cells to differentiate into cells of specific tissues. A broad interest in these areas dates back to the first report of animals produced by in vitro fertilization ("IVF") in 1959, through the first report of the first fertilization of a human egg by IVF in 1968, and the report of the first IVF baby born in England in 1978. However, as a result of interest in developing innovative cell replacement strategies to rebuild tissues and restore critical functions of the diseased or damaged human body, some studies in these areas have more recently focused on the derivation and culturing of "stem cells," and more particularly on human stem cells.

A stem cell is a cell that has the ability to divide (self replicate) for indefinite periods, often throughout the life of the organism. Under the right micro-environmental conditions, or given the right signals, stem cells can give rise ("differentiate") to the many different cell types that make up the organism. That is, stem cells have the potential to develop into mature cells that have characteristic shapes and specialized functions, such as heart muscle, skin cells, hepatic tissues, or nerve cells.

It is widely recognized that a fertilized egg may generate all the cells and tissues that make up an embryo and that support its development in utero. The fertilized egg divides and differentiates until it produces a mature organism which, in mammals, requires the division of cells and their differentiation into more than 200 kinds of cells in the mature organism. These kinds of cells include nerve cells (neurons), blood cells (such as erythrocytes, monocytes, lymphocytes), and bone cells (osteocytes). "Pluripotent" stem cells can give rise to cells derived from all three embryonic germ layers (mesoderm, endoderm, and ectoderm) of an embryo, and much attention has therefore been focused recently on pluripotent stems cells from organisms at early stages of embryonic development. However, ethical concerns have been raised about the use of embryonic cells. As a result, adult (i.e., not embryonic) stem cells have taken on more importance as a source for stem cells for developing innovative therapeutic strategies.

An adult stem ("AS") cell is an undifferentiated (unspecialized) cell that is found in a differentiated (specialized) tissue; it can renew itself and become specialized to yield all of the specialized cell types of the tissue from which it originated, and possibly other specialized cells. AS cells are capable of self-renewal for the lifetime of the organism. Cells capable of differentiating along only one lineage (i.e, "unipotent" cells, which allow a steady state of self-renewal), have been assumed for most tissues of adults until recently. Adult bone marrow cells, for example, have been known and used for decades in transplant therapies. However, even tissues containing only unipotent cells may be repaired if the tissue becomes damaged. When replacement of multiple cell types is required, pluripotent stems cells may become activated to repair the damage. Thus, for several decades stem cells harvested from skeletal bone marrow have been used in therapy in cases of cancer, aplastic anemia, lymphomas, and other life-threatening diseases. Sometimes marrow is transplanted directly from a donor to a patient requiring rescue therapy, and sometimes it is first preserved for a time in liquid nitrogen prior to transplantation.

It was not until recently that researchers have considered the possibility that stem cells in adult tissues could generate the specialized cell types of another type of tissue from that in which they normally reside. However, recent studies have demonstrated that blood stem cells (derived from bone marrow) may be able to generate both skeletal muscle and neurons. This facility of AS cells to generate specialized cell types of another type of tissue has been variously referred to as "plasticity," "unorthodox differentiation," or "transdifferentiation." Presently, there is evidence that AS cells can generate mature, fully functional cells, or that the cells have restored lost function in vivo. Collectively, studies on plasticity suggest that stem cell populations in adult mammals are not fixed entities, and that after exposure to a new environment, they may be able to populate other tissues and possibly differentiate into other cell types.

Most studies on plasticity show plasticity in adult stem cells involving cells derived from bone marrow or brain tissue. Bone marrow appears to contain three stem cell populations, hemoatopoietic stem cells, bone marrow stromal cells, and (possibly) endothelial progenitor cells. Bone marrow stromal cells are a mixed cell population of cells that generate bone, cartilage, fat, fibrous connective tissue, and the reticular network that supports blood cell formation (mesenchymal stem cells of the bone marrow also give rise to these tissues, and may constitute the same population of cells as the bone marrow stromal cells). Studies of hematopoietic stem cells from bone marrow demonstrate an ability to regenerate an entire tissue system, i.e., all cell types found in blood. Thus, bone marrow shows promise as a source for AS cells exhibiting plasticity, and further development of materials and techniques may allow the utilization of all three stem cell populations found in bone marrow.

Efforts are now underway to take advantage of the newly found capability of adult stem cells, with the goal of devising new treatments for disease and disability. Medical science is now providing voluminous evidence of many potential uses for stem cells, such as organogenesis, gene therapy, anti-aging therapies, angiogenesis, organ and tissue repair (particularly in cases of nerve damage), and the treatment of brain tumors, liver disease, and other diseases. AS cells from marrow may now be treated with certain chemicals such as dimethyl sulfoxide (DMSO) and hetastard with PBS, cryopreserved in liquid nitrogen, and later removed, thawed and used for transplantation and other therapies. Today there is new evidence that AS cells may be found in more tissues and organs than previously thought, and that these cells are capable of developing into more kinds of cells than previously imagined. Efforts to devise new treatments for disease and disability utilizing AS cells hold great promise for the future if AS cells may be (i) secured from tissues of the body in a safe, painless, and convenient way, (ii) secured in acceptable quantity, (iii) isolated, (iv) propagated and aggregated ("expanded" via cellular division) to numbers useable for tissue regeneration, (v) and adapted to generate cell types of another type of tissue from that in which they normally reside.

The present invention is directed to the identification of a source of AS cells and other cells within a tissue and organ of the body, and a method for removal of such cells safely and conveniently, by a means which maintains a sterile field, so that the cells may be set aside for isolation, and in such quantity as to be use for propagation to numbers and forms usable for tissue regeneration. Such removal of cells from the body using the present invention takes place under circumstances which offer the minimum of discomfort, is maximally safe, and may in most cases be undertaken in the normal course of body growth and tissue replacement. The present invention is also directed to an apparatus useful for accomplishing the method of the invention. More specifically, the present invention is directed to the identification of teeth as a source of a variety of cells useful for therapeutic purposes (AS cells and other cells useful for medical purposes, such as dendritic cells and precursor cells, collectively "Useful Cells"), the removal of teeth under controlled conditions to preserve sterility, and the further removal of the pulp within such teeth (these processes collectively, "Harvesting"), so that Useful Cells within such teeth may be subsequently isolated and utilized for tissue repair or regeneration.

A number of schemes have been devised to extract human bone marrow. Such schemes employ methods and apparatus applied at various locations of the human skeleton or soft tissue. Published scientific papers, including the recent paper from the National Institute of Health entitled Stem Cells: Scientific Progress and Future Research Directions (June 2001), indicate that sources of AS cells include bone marrow, peripheral blood, blood vessels, the cornea and the retina of the eye, brain, skeletal muscle, dental pulp, liver, skin, the lining of the gastrointestinal tract, and pancreas. Methods and apparatus have been developed to remove stem cells from some of these areas of the human body. As to removal of stem cells from bone material specifically, such methods and apparatus include:

U.S. Pat. No. 5,913,859 to Shapira, which discloses an apparatus for extracting bone marrow from the jawbone of a patient before, during, or after dental procedures.

U.S. Pat. No. 6,110,176 to Shapira, which discloses a method for extracting bone marrow from the jawbone of a patient before, during, or after dental procedures.

In addition, bone marrow collection for transplantation purposes is often accomplished by inserting a needle into a donor's hip or pelvic bone. A needle is inserted into the bone approximately 25 to 30 times through several small incisions made in the pelvic area. Each insertion of the needle takes a "core," which may be aspirated through the needle. The extraction process typically lasts at least one hour or more, or until approximately 1,000 to 1,500 milliliters of the donor's marrow and blood is withdrawn. The donor of the donated marrow requires hospitalization, but may recover fully in a few weeks after the procedure. However, the extraction process is painful, and the patient may feel fatigued for a period of time after the procedure is performed. Further, the procedure requires general anesthesia in an operating theater. This type of device is also frequently used at bedside as a means of taking small biopsy samples using a single coring of the ilial crest. Bone marrow may also be obtained by similar methods from the sternum, or from long bones such as the tibia or femur in adolescents, or other methods having similar drawbacks.

Thus, there is a need for extraction methods that avoid the considerable inconvenience and discomfort of current methods, and apparatus to accomplish such methods, so that AS cells may be secured for use, and for isolation and propagation of AS cells for the medical benefits to be derived for donors and other patients. While the inventions disclosed in these prior patents, methods, and articles fulfill their respective objectives, these prior patents do not describe or suggest a method or apparatus designed to utilize AS cells, and other cells, found in teeth. These prior methods and apparatus of the prior art are directed to securing bone marrow from skeletal tissues, including areas of the skeleton closely associated with dentition, but not from the dentition itself. That is, nothing in the prior art refers to any method for obtaining tissue from teeth in order to produce AS cells for tissue repair or replacement, or other purposes (such as research). No apparatus of the prior art is constructed to achieve this result. Further, the prior art, to the extent it is used to secure marrow from bone, is directed to main skeletal components only, that is iliac (pelvic) bones, long bones, the skull, and connective tissues, all of which tissues the body must replace or repair after marrow is removed. Accordingly, no prior method of marrow removal may be employed without some trauma and increased risk to the donor or patient, or both. Using the method of the present invention, on the other hand, a user may conveniently secure tooth pulp from a patient at the time of normal tooth loss during growth, or during dental work in which teeth are removed, or routinely maintained (such as drilling for a "root canal"), which patient may then receive the benefits derived from that pulp, including any benefits derived from his or her own AS and other cells. Significantly, a user may, using the method of the present invention, take tooth pulp, from which AS cells may be secured, and apply those cells which may exhibit plasticity to the benefit of other individuals, and to the repair or regeneration of a variety of tissue types within the donor or such other individuals.

Moreover, the pulp secured from the donor's teeth may be utilized by isolating from it dendritic and other cells, which may then be utilized in therapeutic treatment for their ability to detect hostile or foreign proteins. Further, AS cells may be a particularly good source of genetic material for gene therapy (in, e.g., the production of "genomic pharmaceuticals"), and in genotyping for donor registration and donor matching. Finally, teeth are not affected by the soft tissue or hard tissue tumors of other parts of the body, including tumors of the jaw, even after metastasis of such tumors. Accordingly, it may be possible to take teeth from a patient prior to administering chemotherapy or radiotherapy in the treatment of cancer in other parts of the body. It may then be possible to autograft the expanded AS and other cells harvested from those teeth back into the patient. By such a procedure, it may be possible to thereby reintroduce into the patient his or her own "fresh," non-cancerous regenerative cells. Such cells, as with bone marrow "rescue" therapy, have not have been exposed to the damaging effects of chemotherapy and radiotherapy, and so are unaffected by such therapies. However, such cells are less likely to have tumorous or metastasized tissues which could then repopulate the patient. All such benefits are derived from the present invention, which provides for securing AS and other cells without trauma, usually at a time convenient to the donor, and generally in a sterile field without significant possibility of contaminating the cells so secured.

In this respect, the method of the present invention substantially departs from pre-existing methods of the prior art, and all apparatus associated with methods of the prior art, and in so doing provides the user with a means for harvesting stem cells (and other cells which may be found in teeth and applied for medical purposes) from the pulp of teeth. By using the invention disclosed herein, users gain the highly desirable ability to secure AS cells for present or future use for tissue regeneration or replacement, while avoiding trauma and long recovery, contamination of the pulp, risk of infection of and by the donor, and other problems associated with extracting marrow from other parts of the body.

DISCLOSURE OF INVENTION

SUMMARY OF THE INVENTION

The present invention overcomes the problems and disadvantages of the prior art by utilizing pulp from teeth, a location from which AS cells (and other cells) have not before now been obtained for medical purposes.

A normal tooth contains living tissue known as "dental pulp." This tissue occupies a canal extending from the apex of the tooth root (or roots), where it communicates with the bone in which the tooth is anchored (the mandible on the lower part of the mouth, and the facial maxillae on the upper part of the mouth), to the area immediately under the crown of the tooth. The canal in each tooth is relatively narrow in and near the root apex, but widens out near the crown into a pulp chamber, which is an enlarged area accommodating a larger volume of dental pulp than is present in the root. The pulp chamber is therefore the location of the great majority of the dental pulp of the tooth. The volume of dental pulp within the pulp chamber contains sufficient dental pulp to be useful in the process of extracting pulp to obtain the AS cells residing there (or "Harvest" or "Harvesting" such cells) for medical use (and other cells). Locating and Harvesting dental pulp from teeth, and particularly the pulp chamber of teeth, for isolation and use of AS cells and other useful cells, is the purpose and object of both the method and apparatus of the present invention.

Dental pulp comprises nerve tissue, blood vessels, lymphatic tissue, mesenchymal tissues, and, possibly, hematopoietic tissues. Mesenchymal and hematopoietic tissues are known to contain Useful Cells (stem cells, dendritic cells, precursor cells, and [note to look up other known medically useful cells] cells useful for medical purposes), when found in other organs of the body. Such tissues are likely to contain such Useful Cells when found within the dental pulp. As noted above, stem cells harvested from skeletal bone marrow have been used in therapy, to counter disease and to provide tissues for generation of tissues for organ and tissue repair. Using the methods and (or) apparatus of the present invention, dental pulp is an additional source for obtaining AS cells and other Useful Cells and, therefore, Harvesting dental pulp provides an additional means for obtaining such cells.

Because of the small amount of pulp residing within a tooth, the quantity of Useful Cells obtained from individual teeth is quite small. However, recently several companies have devised methods for expansion of the number of AS cells by propagation, so that the numbers of such cells are useable for transplantation and other medical purposes. It may also be possible to combine the dental pulp from two or more teeth, extracted at the same or different times, in order to augment the quantity of cells. Thus, AS cells from dental pulp could be used to save lives and improve the health of both the individual from whom they came (by "autologous" transplant) after such propagation. For such patients, the pulp may be frozen and stored as set forth more fully below, or the pulp may be first processed to isolate Useful Cells, the AS cells then propagated and aggregated to numbers useable for tissue regeneration, and then cryopreserved in liquid nitrogen and stored. The AS cells may also be expanded by cellular division ("propagated"), and used immediately for therapeutic purposes. Accordingly, the dentition of a patient may become the source for AS cells which, once adapted to generate cell types of another type of tissue from that in which they normally reside (i.e., they exhibit "plasticity"), are useful for treatment of that patient's disease, or his or her need for replacement or repair tissue. With sufficiently close histocompatibility (from a close relative for instance) or immunosupressive treatment, dentition taken from a non-patient donor may also become the source of AS cells for other patients (by "allogeneic" transplant). However, the immediate need is for collection of AS cells and other Useful Cells for treatment of the patient-donor.

When a tooth is newly extracted by a dentist, oral surgeon or periodontist, or when a tooth is shed from its socket naturally, it carries with it the living dental pulp which may remain vital for some hours following the removal or release of the tooth, particularly if the tooth is stored under ice. Using the method of the present invention, following removal of a tooth from its socket, or following a natural loss of a tooth, the tooth is first placed briefly into a bath of alcohol or other sterilizing liquid medium. Such sterilizing medium is likely to be damaging to cells of many types, including the Useful Cells residing within the pulp chamber of the tooth, should the medium come into contact with that pulp. However, the sterilizing medium using the method and apparatus of the present invention will generally only come into brief contact with the tissue immediately within the opening of the canal or canals at the apex of the root. Because the opening at the root apex is small, and because the pulp is gelatinous and viscous, the sterilizing medium cannot move into, and so damage, the main part of the pulp found within root or the pulp chamber. Rather, only the exposed surface tissue located at the apex of the tooth root may be damaged by exposure to the medium. As to such surface tissue and bacteria, all or virtually all cells are killed. Thus, the sterile field present at the root tip prior to tooth extraction is preserved or restored, or a sterile field at the root tip is produced if the area of bone surrounding the root apex was not already sterile while anchored in the donor's mouth, or was contaminated as it passed out of its socket. At the same time, the exterior surface of the remainder of the tooth, which is generally teeming with bacteria, virus and fungi, is also sterilized by the sterilizing medium, as bacteria present on that surface (and everywhere on the exterior surface of the tooth) is exposed to the same sterilizing medium. As the main part of the dental pulp residing in the pulp chamber is already generally sterile, the result of placing a newly removed tooth into sterile medium is to produce a sealed (within the hard exterior tooth surfaces), sterile field around the tooth, within which is located sterile dental pulp. After achieving sterilization, the entire tooth may then be placed into a saline solution, Ringer's, or other isotonic solution, thereby washing away or diluting the sterilizing medium and creating a barrier to further contamination. After it is diluted or rinsed away, the sterilizing medium is no longer present, and so cannot be absorbed into the pulp located away from the apex of the tooth root, nor can it seep into the pulp cavity through the root or through accessory canals. As access to the pulp within the pulp chamber and the root is generally only afforded through the root, preserving pulp within the tooth root against damage by rinsing away the sterilizing medium will also preserve the pulp within the pulp chamber distal to the apex of the root.

The preferred amount of time for a tooth to rest within a container of sterilizing medium will depend generally on the properties of the medium. At the least, the tooth should remain in the medium for a time sufficient to kill most bacteria normally found in the mouth. On the other hand, the tooth should remain in the medium for a time short enough to avoid significant pulp loss from the apex of the tooth root. The optimal time for a tooth to rest in a sterilizing medium may therefore be as little as one second, or as great as about one hour depending on the medium used. However, for alcohol as a medium, and with access to the pulp within the interior of the tooth only through the apex of the root assumed, the preferred time for a tooth to rest in a sterilizing medium falls within a range of approximately one (1) to five (5) minutes, depending on concentration.

Harvesting the dental pulp from a tooth requires dissecting or opening the tooth to reveal the pulp, or otherwise manipulating the pulp to remove it from the pulp chamber and root. In its simplest form, the method of the present invention comprises the steps of (1) removing a tooth from the mouth of a human, or gathering such a tooth as it is shed, (2) sterilizing the tooth, especially the part of the tooth near the apex of its root or roots, (3) dissecting the tooth by breaking it open, and (4) removing the tooth pulp from the hard exterior fragments of the tooth so dissected. While the present invention is specifically directed toward the benefits to be derived from human teeth, the methods and apparatus of the present invention may also be adapted to the same benefits in dogs, cats, mice, and other mammals.

It should be noted, however, that the removal of the pulp using the method of the present invention may take place at various times after a tooth is naturally shed or identified for removal, and various steps may be taken in the process of the present invention in various orders, at various places, and utilizing various tools and solutions. For example, once a tooth has been removed from the mouth of a donor and sterilized, the tooth may be placed in a cool, sterile medium for temporary storage. In such condition the Useful Cells may be utilized immediately, or within a few hours or days in the place where the tooth was removed (generally at a dentist's office) or nearby (generally at a hospital or other location more suitable for medical procedures). At the location of use, then, the tooth may be opened utilizing the method or apparatus of the present invention, and the pulp then processed to isolate from it the AS and other Useful Cells. The Useful Cells may then be expanded via cellular division to numbers useful in the medical technique to be employed, and then introduced to a patient in an acceptable medical procedure. At the location of use, in the alternative, the dental pulp may be then frozen and stored for a longer period of time after the tooth is opened, or the Useful Cells obtained from the tooth may be isolated, expanded by propagation, and then frozen and stored. However, in these steps of the present invention, and in the further steps set forth below, every effort should be made to remove the pulp from the remainder of the tooth fragments within 12 hours, after such time the viability of the Useful Cells may be substantially reduced, and treatment using such cells compromised.

As a further example the timing of the removal of the pulp using the method of the present invention, once a tooth has been removed from the mouth of a donor and sterilized, the tooth may be immediately opened utilizing the method and apparatus of the present invention. Once the pulp is removed from the tooth fragments, the pulp may then be processed to isolate the AS and other Useful Cells from the connective tissue of the pulp, the Useful Cells expanded, and then used in treatment of a patient without transporting them to another facility or freezing them for long term storage.

As yet a further example the timing of the removal of the pulp using the method of the present invention, once a tooth has been removed from the mouth of a donor and sterilized, the tooth may be shipped in a sterile medium to a location for processing and storage, much as cord blood is now transported, treated, and stored at a location separate from both the donor and the patient-recipient. At such location, the tooth may be treated further and frozen, or it may be opened, treated, and the pulp frozen, or it may be opened, treated, the useful cells isolated, and those cells then expanded via cellular division. If the pulp is frozen, cell isolation and propagation may take place at a later time, and the cells so produced then shipped to a location for treatment of a patient. In some cases the cells may not themselves be used, but products of the cells may be used for treatment, such as in gene therapy. If the cells are expanded without freezing of the pulp, then the cells may be frozen and stored, or expanded by propagation and then frozen and stored, for later shipment to and use at a remote location for introduction into a patient. As the cells obtained from teeth using the method and apparatus of the present invention may be utilized to generate entire tissues, and perhaps organs, the cells may be placed within a process of growing such tissues and organs at any point in any of these processes once the cells are in a condition to begin the process of tissue generation. As growing tissues is generally done in a larger facility having the tissue generating capability, it may be convenient to conduct the steps of isolating AS cells, expanding by propagation, and tissue generation at the same centralized facility. Such variation in the series of steps of the present invention would be more typical of those steps taken at a central processing and storage facility, much as cord blood and its components is handled today. A generalized representation of the method of the present invention appears in the form of a flow chart as FIG. 1 appended hereto.

In any case, however, whether AS cells and other Useful Cells are used in the form of dental pulp, or as isolated cells, or as isolated and propagated cells, or as tissue or organs grown from such cells, or as products derived from any of the forgoing, all methods of identifying and producing Useful Cells should be considered to be part of the present invention if such cells are Harvested from teeth. Moreover, whether the cells are used early in their processing, as isolated AS cells for instance, or later in the process, as wholly grown organs for instance, all methods of producing Useful Cells should be considered part of the present invention regardless of the timing of such use if such cells are Harvested from teeth. Further, all methods which use AS cells and other Useful Cells, whether the cells are used fresh or they are frozen, whether the dental pulp is frozen, or the isolated cells frozen, or the propagated cells frozen, or the whole tissue frozen, and whether such cells are cryopreserved in liquid nitrogen as with skeletal marrow and cord blood, or otherwise preserved, should be considered part of the present invention if such cells are Harvested from teeth. Finally, whether the cells are used before freezing or after, or without freezing, before or after isolation or propagation or aggregation, or growth to entire organs, all methods of using the such cells should be considered part of the present invention regardless of the order of the steps taken to produce the desired type and number of cells, and regardless of the location of their isolation, propagation, aggregation, growth, or ultimate use, if such cells are Harvested from teeth.

Given the unusual nature and properties of teeth amongst the places from which Useful Cells may be obtained, it may be appreciated that the method of the present invention is particularly suited for collection and Harvesting of cells useful for treatment of disease, in tissue repair or replacement, or for the production of other beneficial products, such as pharmaceuticals, and in research. Collection may take place long before the need arises for pulp, AS cells, or other Useful Cells. Such early collection will take place, and is more likely to take place than by other means, during the process of tooth loss or tooth extraction. At such times the tooth is often easily lost or removed in the normal course of growth or in routine dental treatment, such as in the removal of teeth to make room for others, as in orthodontics, or to reduce the possibility of dental problems by prophylactically removing a patient's third molars (so called "wisdom teeth" extraction). With respect to children specifically, it is a medical axiom that the younger the stem cells used in therapy (for example "rescue therapy" in cases of cancers), the better the therapeutic outcome. Harvesting the dental pulp of an 8-year old child and preserving it for later use could result in an improved outcome of from 30% to 45% over what would be the outcome were the marrow of a 38-year old donor used (the average age of donors in the United States). Moreover, by utilizing the methods and apparatus of the present invention, particularly as they relate to freezing for long-term storage, a donor-child may obtain and "bank" for use later in life Useful Cells from his or her own teeth at the time of normal loss of "deciduous" teeth as a child. Thus, the process of collecting dental pulp, and the AS cells and other Useful Cells such pulp contains, is easily undertaken, and likely to become as common as routine dental work, particularly in children.

One embodiment of the apparatus of the present invention comprises a vessel into which a tooth may be placed. The bottom of the vessel in such embodiment is formed to create an elongated, generally "v-shaped" bottom, or a "trough" with narrow bottom. The vessel may have within it a fluid, such as simple saline solution, Ringer's, or other isotonic solution, for the protection of the tooth to be dissected, and the pulp within the tooth once dissected. As the method of the present invention requires the sterilization of the subject tooth with a sterilizing medium, the fluid within the vessel may provide such protection of the tooth by first providing a wash, or dilution of, the sterilizing medium. Additionally, when the tooth has been dissected, the pulp within the tooth would be exposed to air unless such a neutral solution is used to isolate the pulp from the environment. An isotonic solution, at normal body temperature or below, will preserve the now accessible pulp from dessication, contamination, or other damaging exposure to air. Accordingly, such an isotonic solution, in a quantity sufficient to cover the tooth prior to dissection should be used in conjunction with the apparatus of the present invention.

Two of the sidewalls of the vessel in such embodiment join the sides of the bottom. Accordingly, a tooth placed within the vessel will fall in response to gravity until it rests on the bottom of the vessel and, as the sides of the v-shaped bottom narrow and join near the elongated center of the bottom, the arrangement of sidewalls and v-shaped bottom of the vessel allow a tooth placed within the vessel to fall within the vessel until the tooth comes up against the opposite side of the bottom where the sides meet at the apex of the v-shaped bottom. In such position, the tooth will come to rest so that it falls to, and comes to rest within the apex of the bottom, and the tooth will in further response to gravity and the fluid within the vessel tend to come to rest so that the major axis of the tooth is oriented longitudinally, along and parallel to the length of the lowest portion of the v-shaped bottom, and as low within the trough as the width of the trough will allow. In such position, a tooth is in a good position to open evenly in response to pressure which may be exerted by the apparatus. In such position, the tooth is "clamped" into position by the v-shaped bottom so it cannot roll to the side of the bit, but the tooth fragments are free to fall aside and not damage or compress the pulp.

A wedge-shaped splitting bit is provided in the apparatus of the present invention, arranged to move within the vessel toward the apex of the bottom of the vessel. The bit is arranged so that it may so move until it bears against a tooth residing within the trough of the vessel's bottom. The splitting bit may be shaped to fit tightly within the bottom of the vessel, the apex of the bit matching the apex of the trough, so as to run tightly along and within the corresponding length at the apex of the bottom trough. However, in other embodiments of the present invention, the angle at the edge of the splitting bit may be either more or less acute than the trough (i.e., the bit may narrow to an edge more quickly than the bottom of the trough at the bottom of the vessel), or it may present a relatively flat face toward a tooth residing at the bottom of the trough. In yet other embodiments, the bit may have projections which may extend from the leading edge or face of the bit, so as to apply pressure to a very small area of the tooth residing at the bottom of the trough.

The splitting bit is situated within the vessel when in use, and held tightly against movement perpendicular to the length of the trough at the bottom of the vessel. Such restriction of movement is accomplished in one embodiment by guide tracks running from a position near the opening of the vessel to a position near the bottom of the trough, which tracks constrain movement of the bit perpendicularly to the length of the apex of the trough. Within such tracks, the bit may, in one embodiment of the apparatus of the invention, travel toward the opening of the vessel a sufficient distance to allow a large tooth to come to rest within the trough, and also toward the apex of the bottom of the vessel a distance sufficient to allow the bit to bear against a small tooth. Other embodiments of the apparatus may be manufactured to accommodate different sizes of teeth.

The splitting bit is provided with a means for moving the bit both toward and away from the trough of the bottom of the vessel. In one simple embodiment of the present invention, the means for moving the bit is a supporting shaft formed to create a screw, having an exterior thread, upon the end of which the bit is mounted. In such embodiment, the mounting of the bit on the screw may be accomplished by fixing the bit on the end of the screw so that the bit and screw cannot rotate one against the other. In such embodiment, the screw is advanced toward the trough of the bottom of the vessel by the turning of a "nut" having complimentary (to the screw) interior thread, or by other means having complimentary thread which may engage the screw. The screw or the nut, or both, are appropriately held in position so that the nut may rotate and the screw may advance, but each such component is otherwise constrained. In another simple embodiment of the present invention, the screw means for moving and supporting the bit is rotatably mounted. In such embodiment, the screw is advanced toward the trough of the vessel by the turning of the screw within a nut having complimentary interior thread, or by other means having complimentary thread which may engage the screw. Again, the screw or the nut, or both, are appropriately held in position so that the screw may rotate and advance, but each such component is otherwise constrained.

In yet other embodiments of the apparatus of the present invention, the means for moving the bit is a supporting shaft formed to create a piston or push rod, which may be acted upon by a motor, a cam, a screw, or by hydraulic piston or other means for advancing the piston or push rod toward the trough at the bottom of the vessel. In all of the above arrangements the means for advancing the bit toward the trough at the bottom of the vessel may also be used to withdraw the bit from the trough a distance sufficient to allow the placement of a (large) whole tooth in the apparatus for dissection, and sufficient to allow removal of pieces of the tooth so dissected. All of the above arrangements may also be accomplished without the use of guide tracks if the bit is, except for advancing toward and from the trough of the bottom of the vessel, sufficient constrained against other movement by other appropriate means. Such other means must constrain the bit against movement perpendicular to the advance and withdrawal of the bit, and also restrained against rotating within the vessel.

Most embodiments of the apparatus of the present invention provide, in the means for advancing the bit toward the trough, means capable of generating sufficient force to break a tooth open when the bit is urged against the tooth. By use of such force, a whole tooth may be fractured into two or more pieces, revealing the dental pulp residing within the tooth, and making that pulp accessible to a user for further processing. Such apparatus may be as simple as a diamond cutter's "rig," being no more than the bare essentials of a trough, a mallet, and a chisel. On the other hand, the dissection of a tooth may be accomplished by ultra-sonic means, the frequency and intensity of the ultra-sonic splitter being calculated to cause a disrupting resonation in the hard tooth exterior (and fragments) without undue damage to the pulp or soft cells within the tooth. Most embodiments of the apparatus of the present invention also provide, in the means for advancing the bit toward the trough, a restriction means by which the advance of the bit toward the trough may be controlled, so that the bit does not advance so far as to allow it to crush the tooth, or crush the pulp within the tooth, or crush hard tooth fragments against or into the pulp. However, in the mallet and chisel of the diamond cutter's rig, and in other simple arrangements, the restriction means may be absent, and in such embodiments the risk of damage to pulp and cells within a tooth is increased.

After dissection of a tooth, some of the dental pulp from within may fall away from the hard tooth fragments. In such cases gathering the pulp for later use is easily accomplished. However, after most tooth dissections, much of the dental pulp within the tooth remains attached to hard tooth fragments. A second vessel may be used for removal of the pulp after the tooth is dissected. Such a second vessel may be a simple bath of isotonic solution, fitted with a pulp removal means. Such pulp removal means may be as simple as a tweezer, by which hard fragments may be removed from the pulp, or a burred shaft known as a barbed broach, by which the pulp may be drawn from the tooth fragments. However, a convenient arrangement for separating tooth fragments and pulp consist of a sharp or barbed projection situated on a sloping side of the second vessel, upon which the dissected tooth may be worked. In so working, the user would present a hard tooth fragment having pulp to the projection so as to catch the pulp on the projection. The user thereafter may pull the hard tooth fragment away from the projection, leaving the pulp on the projection or allowing it to fall off the projection and toward the bottom of the second vessel. Pulp remaining on the projection may be brushed off, or a separate means may be used to disengage the pulp from the projection, so that pulp remaining on the projection after working the hard tooth fragment against the projection also may fall off the projection and toward the bottom of the second vessel. Proceeding from a first tooth fragment to a second tooth fragment, if necessary, and so on to other tooth fragments, a user may conveniently pull virtually all pulp from the hard tooth fragments of a single donor. The sides of the second vessel may be sloped sufficiently to allow the pulp to fall toward the center of the second vessel, which may be fitted with a pit, for receiving a screen, and a screen with handle for formed to fit within the pit. Once the pulp from a donor falls into the center of the second vessel and into the screen, the screen may then be used to transport the pulp to another vial containing anti-coagulant, such as EDTA, heparin, or other anticoagulant, to retard coagulation, and to mix the pulp with appropriate chemicals for freezing in liquid nitrogen. The pulp may then also be transported to other locations for further manipulation and use using the screen of the second vessel or other means.

Utilizing the method of the present invention to identify teeth as the source of dental pulp from which Useful Cells may be Harvested, and thereafter isolated, expanded via cellular division, and used for medical and research purposes. Prior to the present invention no method is know for such identification and Harvesting of dental pulp from dentition of a patient or other donor, in order to use the pulp so secured, and the stem cells and other cells contained in the pulp, for beneficial medical purposes. Further no method allows extraction of pulp from within extracted while preserving a sterile environment to avoid contamination of the pulp, and trauma and infection of the donor. Utilizing the apparatus of the present invention, a user may employ such apparatus to practice the method of the present invention to advantage conveniently, and without such contamination, trauma, and infection. It may therefore be appreciated that the present invention holds advantages not found in any other existing methods or apparatus of the prior art, as the invention is specific to Harvesting of Useful Cells from an organ of the body which may be, and often is, discarded during childhood or routine dental work, and so carries with it the advantages related to Harvesting from such "expendable" organ.

OBJECTS OF THE INVENTION

A principal object of the present invention is to identify human and other mammalian teeth as organs of the body from which Useful Cells may be Harvested, as an alternate source of cellular material to be used in therapeutic treatment and research, and provide a method and apparatus for Harvesting teeth for such purposes.

A further principal object of the present invention is to identify Useful Cells from teeth as cellular material which may be Harvested and expanded, and used medically for treatment of disease, tissue regeneration, and tissue replacement, and provide a method and apparatus for Harvesting teeth for such purpose.

A further object of the present invention is to provide a method and apparatus for Harvesting Useful Cells from organs of the body which avoids trauma and long recovery of the donor of such cells.

A further object of the present invention is to provide a method and apparatus for Harvesting Useful Cells from the body in such fashion as to promote a sterile field during such Harvesting.

A further object of the present invention is to provide a method and apparatus for Harvesting Useful Cells from the body while avoiding contamination and degradation of the cellular material obtained in such Harvesting.

A further object of the present invention is to provide a method and apparatus for Harvesting Useful Cells from the body while avoiding medical risks, including risk of infection of the donor in the Harvest, risk of infection of a patient by contamination of cells Harvested from the donor, and other problems associated with extracting marrow from other parts of the body.

A further object of the present invention is to provide a method and apparatus for Harvesting Useful Cells from the body having the unique characteristic of being preserved against contamination and degradation within the sealed environment of the hard tooth exterior, and to preserve such characteristic throughout processing, to result in uniquely viable medically useful cells, and unique products arising therefrom.

A further object of the present invention is to provide a method and apparatus for Harvesting Useful Cells from a patient before the need arises for such cells, so that Useful Cells may be treated and manipulated to produce cells of a kind, and in an amount, useable for treatment of that patient.

A further object of the present invention is to provide a method and apparatus for Harvesting Useful Cells from a patient before the need arises for such cells, so that Useful Cells may be treated and manipulated to produce cells useable for treatment of that patient which have not been affected by medical treatments normally destructive to the cells and tissues of that patient.

A further object of the present invention is to provide a method and apparatus for Harvesting Useful Cells from a donor which may be treated and manipulated to produce cells of a kind, and in an amount, useable for treatment of a patient other than the donor.

BRIEF DESCRIPTION OF DRAWINGS

The accompanying drawings, which are incorporated in and constitute a part of this specification, illustrate one embodiment of the present invention and, together with the description, serve to explain the principles of the invention.

DETAILED DESCRIPTION OF A FIRST PREFERRED EMBODIMENT

Figure 1:
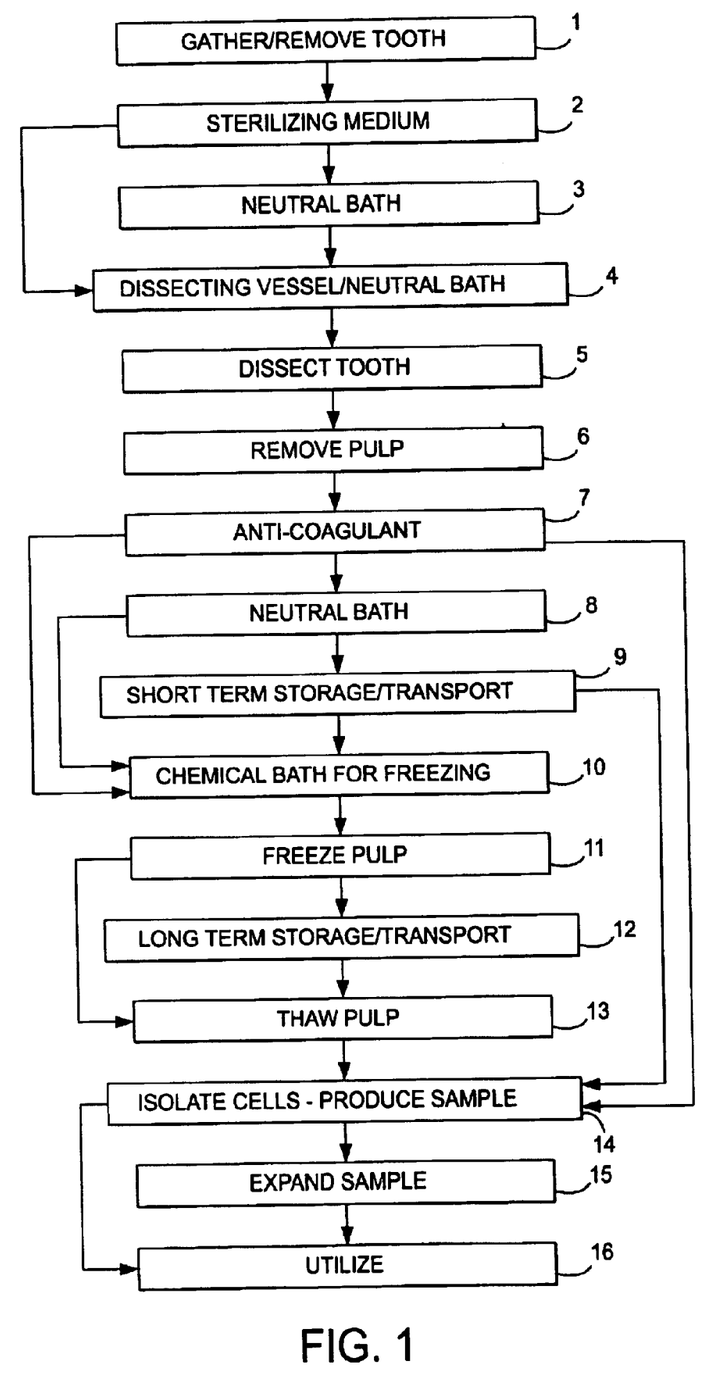
FIG. 1 is a flow chart diagram of one embodiment of the method of the present invention, as it may be practiced when freezing of dental pulp is desirable, including the major steps of obtaining a tooth, sterilizing the tooth, dissecting the tooth, and removing the pulp from within the tooth.

Referring initially to FIG. 1, the steps in the method of the present invention are shown in flow-chart form. FIG. 1 shows such steps in circumstances where it is most desirable to freeze the pulp extracted from a tooth, rather than the tooth itself or the isolated cells obtained from the tooth. Such circumstances may exist where the medium for sterilization and means for dissection of the tooth are each close or at hand, but the facility for isolation of cells from the pulp is distant. Thus, it may be possible to supply a dentist with a kit for sterilization utilizing the apparatus of the present invention, but the isolation of cells from the pulp obtained and treated by the dentist is best done at a hospital or "cell bank."

In FIG. 1, a tooth identified for removal is extracted by a dentist 1, or gathered after it is naturally shed 1. After securing the tooth 1, the dentist or parent or other responsible person places the tooth into a sterilizing medium 2. It should be noted here that throughout the various embodiments of the methods of the present invention, a short-term storage or transport of materials is involved. For example, between the extraction of a tooth 1 and the placing of it in a sterilizing medium 2, the dentist in some sense temporarily "stores" the tooth in his hand or dental tool, and transports it to the sterilizing medium. Other temporary "storage" and transport activities may take place between these steps, and between other steps of these methods, however the viability of the living cells within the tooth, and so the efficacy of the treatment using such cells, degrades quickly with time. Accordingly, while such temporary "storage" may occur using the methods of the present invention, such temporary "storage" should be minimized. To present the methods of the present invention more clearly, such temporary "storage" does not appear in FIG. 1 or elsewhere.

Returning to FIG. 1, the tooth obtained by the dentist is generally placed in a cool, isotonic bath 3 after removing it from the sterilizing medium, and then placed in a dissecting vessel 4, such as the dissecting vessel of apparatus of the present invention. The isotonic bath may comprise saline solution or Ringer's solution, or other desirable solution useful for washing the sterilizing medium from the tooth, or diluting the medium. As the dissecting vessel also contains a cool, isotonic solution, the step of placing the tooth in the neutral bath 3 may in some cases be skipped. However, the solution of the neutral bath 3 may also contain anti-coagulant or other chemicals which may be useful, but which may best be washed from the tooth, or seriously diluted, prior to dissection. Continuing with FIG. 1, after the tooth is placed in a dissecting vessel 4, the tooth is then dissected 5 (i.e. the tooth is broken, leaving hard tooth fragments and tooth pulp). Again, the apparatus of the present invention may be used for such dissection. After dissection 5, the pulp is removed from the hard tooth fragments 6, perhaps utilizing the apparatus of the present invention. After the pulp is removed from the tooth, the pulp is then generally placed immediately into a solution containing anticoagulant 7 and, if the pulp is to be stored for a short period of time or transported, again into a neutral bath 8, and then on to such short-term storage or transport 9.

In the embodiment of the method of the present invention appearing in FIG. 1, it is envisioned that the pulp will be frozen, or at least the user maintains the option to freeze the pulp. Accordingly, after the pulp emerges from short-term storage 9, or after the pulp is removed from the neutral bath 8 or the anti-coagulant bath 7, the pulp may then be placed in a solution containing chemicals such as dimethyl sulfoxide (DMSO) and hetastard with PBS 10, which reduce damage to the pulp when it is frozen 11. The pulp may then be frozen 11 (and cryopreserved in liquid nitrogen) and stored for a greater or lesser time 12 (up to many years), or transported while frozen 12 to another location. At the end of such storage or transport, the pulp may then again be thawed 13 so that is again ready for manipulation to isolate the Useful Cells 14. While this embodiment of the method of the present invention envisions retaining the option to freeze the pulp 11 after a suitable chemical bath 10, the user also has the option of processing the pulp fresh if the time from emersion in anti-coagulant solution 7 directly to the time of isolation of Useful Cells 14 is not too great. In the alternative, the user retains the option of processing the pulp fresh if the time from placing in short-term storage 9 to the time of isolation of Useful Cells 14 is not too great. In any case the user, in the isolation of Useful Cells 14, thereby produces a sample of Useful Cells 14, sufficient in size to be expanded by expanded via cellular division 15 and then utilized in research and medical treatment 16, or utilized 16 directly without such expansion.

Figure 2:
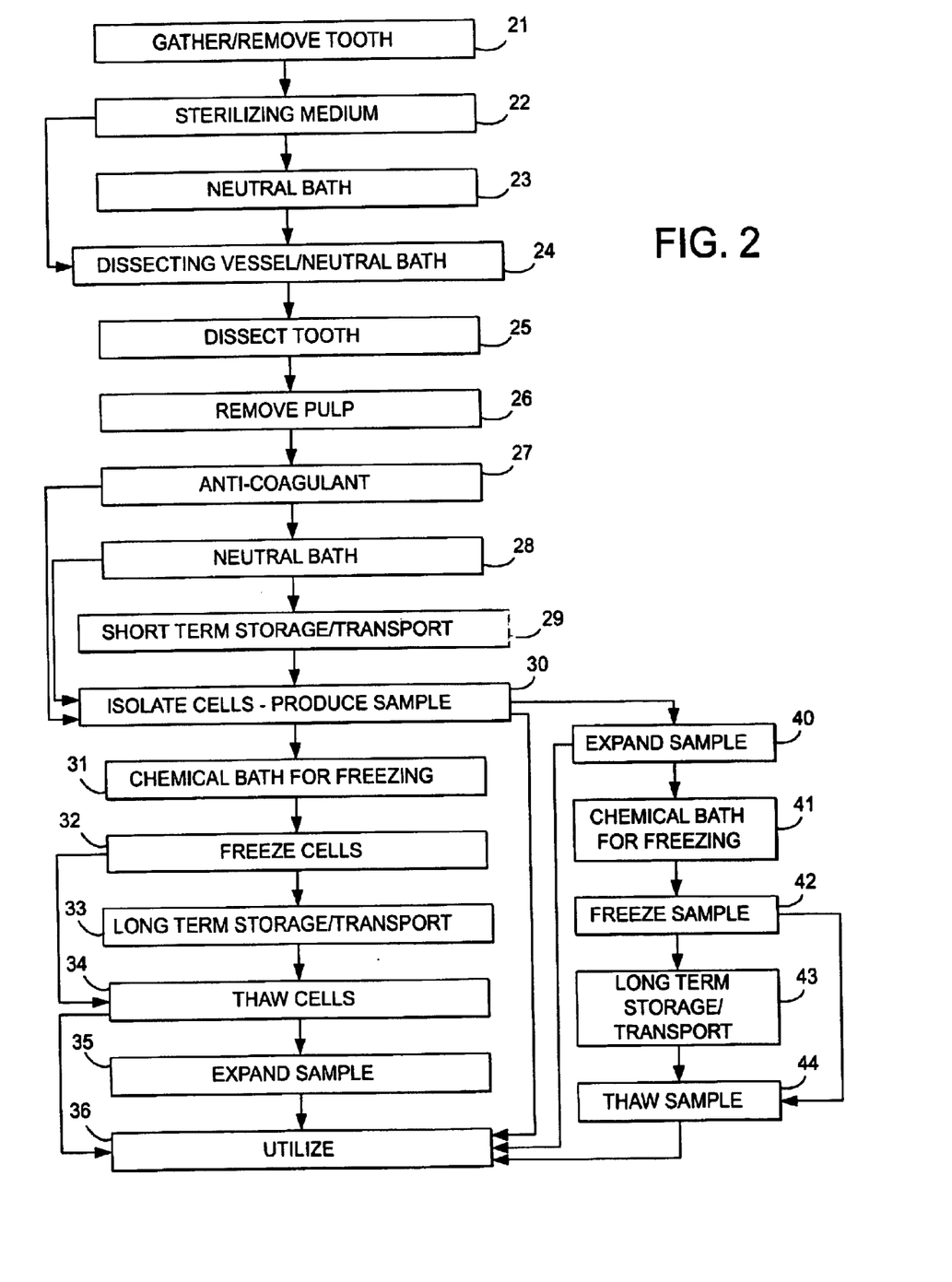
FIG. 2 is a flow chart diagram of a second embodiment of the method of the present invention, as it may be practiced when freezing of isolated cells is desirable, including the major steps of obtaining a tooth, sterilizing the tooth, dissecting the tooth, and removing the pulp from within the tooth.

Referring now to FIG. 2, alternate steps in the method of the present invention are shown in flow-chart form. FIG. 2 shows such steps in circumstances where it is most desirable to freeze the Useful Cells already isolated from the pulp of a tooth, rather than freeze the tooth itself or the pulp obtained from the tooth. Such circumstances may exist where the medium for sterilization and means for dissection of the tooth are each close or at hand, along with the capability for isolating Useful Cells from the pulp. Thus, it may be possible to extract a tooth in a hospital or a "cell bank," subject it to sterilization and dissect the tooth utilizing the apparatus of the present invention, and isolate and treat the Useful Cells from the pulp so obtained all at one location.

In FIG. 2, a tooth identified for removal is extracted by a technician 21, or gathered after it is naturally shed 21. After securing the tooth 21, the technician places the tooth into a sterilizing medium 22. The tooth obtained by the technician is again generally placed in a cool, isotonic bath 23 after removing it from the sterilizing medium, and then placed in a dissecting vessel 24, such as the dissecting vessel of the present invention. The isotonic bath may be comprised of saline solution or Ringer's, or other desirable solution useful for washing the sterilizing medium from the tooth, or diluting it. As the dissecting vessel also contains a cool, isotonic solution, the step of placing the tooth in the neutral bath 23 may in some cases be skipped. However, the solution of the neutral bath 23 may also contain anticoagulant or other chemicals which may be useful, but which may best be washed from the tooth, or diluted, prior to dissection. After the tooth is placed in a dissecting vessel 24, the tooth is then dissected 25 (broken into fragments and pulp). Again, the apparatus of the present invention may be used for such dissection. After dissection 25, the pulp is removed from the tooth 26, perhaps utilizing the apparatus of the present invention. After the pulp is removed from the tooth, the pulp is then generally placed immediately into a solution containing anti-coagulant 27 and, if the pulp is to be stored for a short period of time or transported, again into a neutral bath 28, and then on to such short-term storage or transport 29.

In the embodiment of the method of the present invention appearing in FIG. 2, it is envisioned that the isolated Useful Cells will be frozen, rather than the pulp, or at least the user maintains the option to freeze the Useful Cells. Accordingly, after the pulp emerges from short-term storage 29, or after the pulp is removed from the neutral bath 28 or the anti-coagulant bath 27, the Useful Cells within the pulp are isolated 30 and a sample of such cells thereby produced 30. The sample of isolated Useful Cells may then be placed in a solution containing chemicals, such as dimethyl sulfoxide (DMSO) and hetastard with PBS 31, which reduce damage to the cells when the sample is frozen, and the Useful Cells then frozen 32 for long-term or short-term storage 33, or transported while frozen to another location 33, or both. At the end of such storage or transport, the pulp may then again be thawed 34 so that is again ready for manipulation to expanded the Useful Cell sample 35 via cellular division, for eventual utilization in treatment 36.

While this embodiment of the method of the present invention envisions retaining the option to store and transport 33 the Useful Cells 32 after a suitable chemical bath 31, and freezing them 32 as depicted in FIG. 2, the user has the option of thawing 34 the Useful Cells without storage or transport 33. The user also retains the option of utilizing 36 the Useful Cells in research or treatment after thawing 34 of a sample, without separate expansion 35. In any case the user, in the isolation of Useful Cells 30, thereby produces a sample of Useful Cells 30, sufficient in size to be expanded by expanded via cellular division 35, and then utilized in research and medical treatment 36, or utilized 36 directly, without such expansion 35.

Moreover, a user has the additional option in this embodiment of the present invention, as depicted in FIG. 2, of expanding the Useful Cells 40 via cellular division after isolation 30, and then proceeding to steps for freezing the expanded sample. Once expanded, therefore, the Useful Cells may be placed in a chemical bath of, for instance, dimethyl sulfoxide (DMSO) and hetastard with PBS preparatory to freezing 41, the sample frozen 42, and then placed into storage or transported 43, the sample thawed 44, and the sample utilized 36 in research or in treatment. As before, the user retains the option to thaw the expanded sample 44 after freezing 42 without either storage or transportation to another location 43. The user also retains the option of processing fresh Useful "Cells after isolation 30, utilizing the Useful Cells 36 directly, or expanding the Useful Cells 40 by cellular division and then utilizing the Useful Cells 36 directly. Such treatment by the user in FIG. 2 corresponds to the "rush" utilization 36 of fresh Useful Cells without any freezing of the Useful Cells 32 or freezing of an expanded sample 42.

Figure 3:
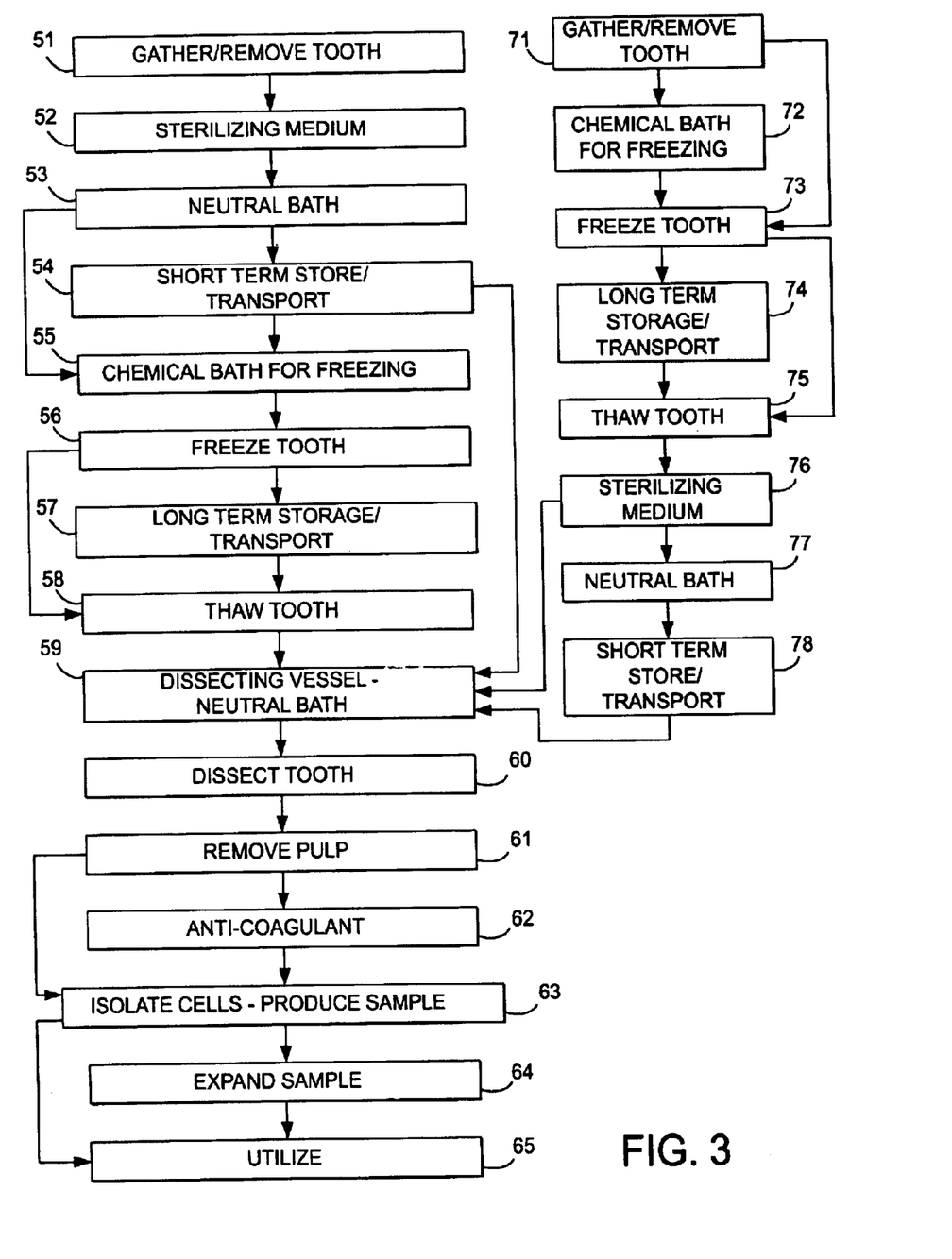
FIG. 3 is a flow chart diagram of a third embodiment of the method of the present invention, as it may be practiced when freezing of one or more teeth is desirable, including the major steps of obtaining a tooth, sterilizing the tooth, dissecting the tooth, and removing the pulp from within the tooth.

Referring now to FIG. 3, alternate steps in the method of the present invention are shown in flow-chart form. FIG. 3 shows such steps when it may be desirable to preserve a tooth under circumstances where the means for freezing may be unavailable at the site of tooth removal or natural tooth loss, or other circumstances where dissection of the tooth may be delayed. Such circumstances may exist where the tooth is lost while hiking, for instance, when the means for dissection of the tooth are located elsewhere, but the user has brought vessels containing medium for sterilization and a neutral bath. Thus, it may be possible to lose a tooth while on such a hike, subject it to sterilization and neutralization, and return with the tooth for later dissection of the tooth utilizing the apparatus of the present invention at home, in a hospital, or in a "cell bank."

In FIG. 3, a tooth identified for removal is extracted 51, or gathered after it is naturally shed 51. After securing the tooth 51, the tooth is placed into a sterilizing medium 52, and then again generally placed in a cool, isotonic bath 53 after removing it from the sterilizing medium. In such condition, while covered with such neutral solution 53, the tooth may be stored for a relatively short period of time 54, or transported to another location 54, or both. In the embodiment of the methods of the present invention appearing in FIG. 3, it is envisioned that the tooth will be frozen, rather than the pulp or the Useful Cells, or at least the user maintains the option to freeze the tooth. Accordingly, after the tooth emerges from short-term storage 54, or after the pulp is removed from the neutral bath 53, the tooth may then be placed in a solution containing chemicals which reduce damage to the Useful Cells within the tooth 55, such as dimethyl sulfoxide (DMSO) and hetastard with PBS, and the tooth may then be frozen 56. In such condition the tooth may be kept in long-term or short-term storage 57, or transported while frozen to another location 57, or both, and the tooth then thawed 58, so that it may be made ready for dissection and pulp removal. Upon thawing, the tooth should be promptly placed in a dissecting vessel 59, such as the dissecting vessel of the present invention. The isotonic bath of the dissecting vessel may again be comprised of saline solution or Ringer's solution, or other desirable solution useful for maintaining the condition of the tooth. A separate neutral bath containing solution for washing the sterilizing medium from the tooth, or diluting it, is generally not necessary at this stage, as the tooth has already been subjected to such a bath prior to freezing 56. However, the solution of a neutral bath may also contain anti-coagulant or other chemicals which may be useful for washing from the tooth the chemicals contained in the bath preparatory to freezing, or diluting them. Accordingly, a neutral bath (not shown) may be used to advantage after the thawing of the tooth 58 and before placing the tooth into a dissecting vessel 59.

Proceeding from the placement of a tooth into the dissecting vessel 59, the tooth is dissected 60, the pulp from within the tooth removed 61 utilizing apparatus like that of the present invention, the pulp then generally subjected to anti-coagulant 62, and the Useful Cells then isolated from the pulp 63 and a sample produced. The Useful Cells sample may then be expanded 64 via cellular division, and the cells utilized 65 in research or treatment, or the Useful Cells utilized 65 directly after isolation 63. While this embodiment of the method of the present invention appearing in FIG. 3 envisions retaining the option to freeze the tooth 56 after a suitable chemical bath 55, as depicted in FIG. 3, the user also has the option of processing the tooth fresh if the time from emersion in a neutral bath 53 and short-term storage and transport 54 to the time of dissection of the tooth 60 is not too great. While far from optimal handling, the tooth may also be frozen 73 directly after gathering 71, and a tooth may be thawed 75 directly after freezing 73, without storage or transport 74.

Moreover, a user has the additional option in this embodiment of the method of the present invention, as depicted in FIG. 2, of freezing a tooth without sterilization if the capability for freezing is available but an appropriate sterilizing medium is not. In such a process, a tooth is removed or gathered after natural loss 71, subjected to a chemical bath of, for instance, dimethyl sulfoxide (DMSO) and hetastard with PBS, preparatory to freezing 72, the tooth frozen 73, and then placed into storage or transported 74. The tooth may then be thawed 75, subjected to a sterilizing medium 76, washed or rinsed in a cool, isotonic bath 77 to remove or dilute the sterilizing medium, and stored for a short period or transported 78 to a dissecting vessel as before 59. Again, as the dissecting vessel contains isotonic solution, the tooth may in some cases be removed from the sterilizing medium 76 and placed in the dissecting vessel 59 directly, dissected 60, and further processed as before.

DETAILED DESCRIPTION OF A SECOND PREFERRED EMBODIMENT

If the apparatus of the present invention is utilized for obtaining teeth, dissecting such teeth and removing the pulp from within such teeth, a user may Harvest tooth pulp conveniently, while maintaining the viability of the Useful Cells within the pulp, and reducing the risk of contamination of the cells so obtained.

Figure 4:
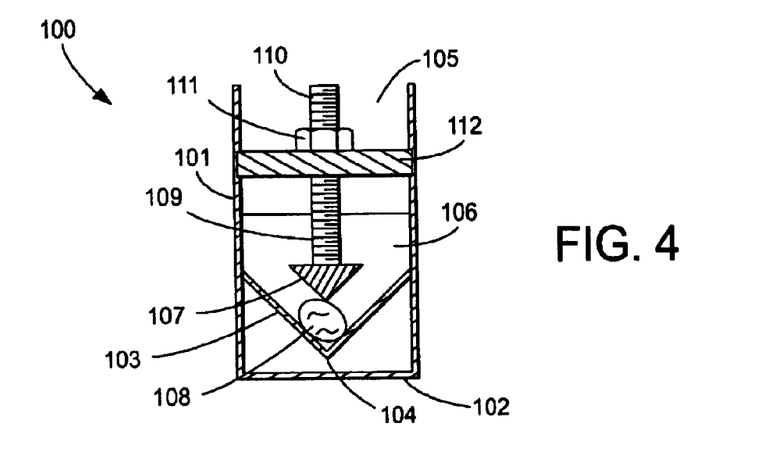
FIG. 4 is a cross sectional diagram of an exemplary embodiment of the dissection vessel apparatus of the present invention, showing an end-view of the v-shaped bottom within the vessel, an end-view of the splitting bit within the vessel, and the splitting bit driving means, wherein a whole tooth resides in the apex of the v-shaped bottom.

Referring initially to FIG. 4, an exemplary embodiment of the apparatus of the present invention is shown in cross section. In FIG. 4, an open-topped dissection vessel 100 is shown, comprised of vertical walls 101 and flat, horizontal bottom 102 for setting flat on a horizontal surface (not shown). The dissection vessel is capable of containing fluids for covering a tooth during and after dissection. Within the dissection vessel 100, a separate v-shaped bottom, or trough, is formed from two flat members 103, the trough having an apex 104 facing the bottom of the dissection vessel 102, and opening toward the open top of the dissection vessel 105. The length of the trough runs from one approximately vertical side 101 of the dissection vessel to the other approximately vertical side 101 of the dissection vessel. Within the dissection vessel 100, the two flat members 103 of the trough are also formed to smoothly intersect the approximately vertical sides 101 of the dissection vessel 100 around all edges of such flat members 103, thereby creating a smooth transition from the sides of the dissection vessel 100, on to the two flat members 103. Accordingly, an object, such as a tooth, placed anywhere within the dissection vessel will, if allowed to fall within the vessel, fall onto one of the two flat members 103, and not be held by any obstacle within the dissection vessel, until the object comes to rest within the apex of the trough 104 at its lowest point, where the flat members meet at the apex of the v-shaped trough.

The dissection vessel 100 has within it a fluid 106, such as simple saline solution, Ringer's solution, or other isotonic solution, for the protection of the tooth to be dissected. As the method of the present invention requires the sterilization of the subject tooth with a sterilizing medium, the fluid within the vessel may provide such protection of the tooth by first providing a wash, or dilution of, the sterilizing medium. The fluid 106 within the dissection vessel 100 also assists a tooth placed within the dissection vessel to come to rest so that a major axis of the tooth is oriented longitudinally, along and parallel to the length of the lowest portion of the trough, and as low within the apex 104 of the trough as the width of the trough will allow. In such position, a tooth is in a good position to open evenly in response to pressure which may be exerted by the apparatus. The fluid within the dissection vessel has the additional purpose of protecting the pulp once it has been removed from the tooth, as pulp within the tooth would then be exposed to air unless such a cool, neutral solution, is used to isolate the pulp from the environment, and so preserve the pulp from dessication, contamination, or other damaging exposure to air. The isotonic solution is placed within the dissection vessel in a quantity sufficient to cover the tooth prior to dissection.

Referring again to FIG. 4, a wedge-shaped splitting bit 107 is provided in the apparatus of the present invention, arranged to move within the vessel toward the apex 104 of the bottom of the trough, and so far as to bear against a tooth, should one reside within the apex 104 of the trough. The splitting bit 107 is shaped in this embodiment to fit tightly within the apex 107 of the trough of the vessel, the apex of the bit 107 matching the apex 104 of the trough, so as to run tightly along and within the corresponding length at the apex 104. The splitting bit 107 is situated within the vessel when in use, and held tightly against movement perpendicular to the length of the trough at the bottom of the vessel. In this embodiment, the bit 107 may travel toward the opening of the vessel 105 a sufficient distance to allow a (large) tooth 108 to come to rest within the apex 104 of the trough, and between the bit 107 and the apex 104 of the trough, and also travel toward the apex 104 of the trough a distance sufficient to allow the bit to bear against a (small) tooth 108. The splitting bit 107 is in this embodiment provided with a supporting shaft formed to create a screw 109, having an exterior thread 110, upon the end of which the bit 107 is fixedly mounted. A "nut" 111 is provided, in this embodiment, with complimentary (to the screw) interior thread (not shown). The screw shaft 109 in this embodiment is held in position by a vessel closure 112, so that the nut 111 may rotate on the screw shaft 109 on the top of the closure 112, thereby advancing the screw shaft 109 into the dissecting vessel 100, and toward and into a tooth 108 held captive in the apex 104 of the trough. The vessel closure 112 also operates to withdraw the screw shaft 109 out of the dissecting vessel 100, and away from the tooth 108 when dissection of the tooth is complete. The vessel closure 112 is held within the dissection vessel 100 by engagement of threads (not shown) around its perimeter with complementary threads in the opening of the dissection vessel 100, or by other appropriate means. The nut 111 is also provided with a bearing means for holding the nut against the closure 112 during operation. Thus, as shown in FIG. 4, a user may place a tooth 108 within the dissection vessel 100, close the vessel using the closure 112, and allow the tooth 108 to fall, and come to rest within the apex 104 of the trough.

Figure 5:
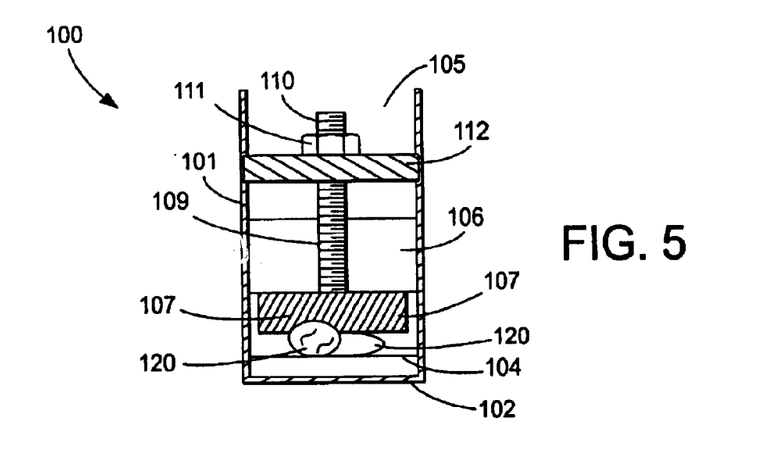
FIG. 5 is a cross sectional diagram of an exemplary embodiment of the dissection vessel apparatus of FIG. 4, showing a side-view of the v-shaped bottom, a side-view of the splitting bit, and the driving means, wherein the tooth of FIG. 4 has been dissected.

Referring now to FIG. 5, once the tooth 120 falls to the apex 104 of the trough, the tooth will likely orient itself so that its major axis is parallel with the length of the apex 104 of the trough. In such position, the tooth 120 is trapped in the lowest position within the trough, and a force exerted from above is therefore not likely to further move the tooth within the trough. The tooth 120 is therefore in position in the dissection vessel 100. The user may then operate the nut 111 to engage the complimentary screw of the screw shaft 109 as if FIG. 5, thereby advancing the screw shaft 109, and the splitting bit 107 attached thereto, toward and into a tooth 120 residing within the apex 104 of the trough, thereby applying sufficient force along the apex of the splitting bit 107 to break the tooth 120.

Figure 6:
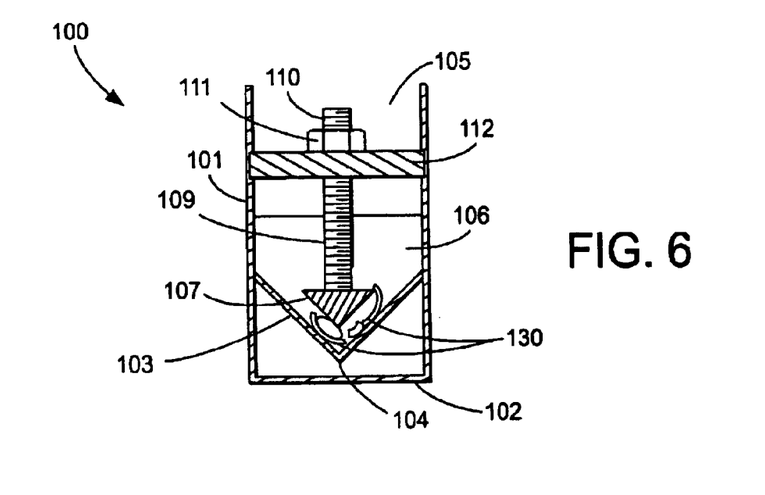
FIG. 6 is a cross sectional diagram of an exemplary embodiment of the dissection vessel apparatus of FIG. 4 and FIG. 5, showing an end-view of the v-shaped bottom, splitting bit, and driving means, wherein the restriction means controlling the advance of the bit toward the trough in the v-shaped bottom has stopped the advance of the bit, thereby preventing the crushing of the tooth and pulp.

Referring now to FIG. 6, when sufficient force is applied by the splitting bit 107, the tooth is broken into hard tooth fragments, pulp, and hard tooth fragment to which pulp is clinging (collectively, 130). The user may then withdraw the screw shaft 109 and splitting bit 107 from the trough, moving it toward the opening 105 of the dissecting vessel, thereby providing room for removal of the tooth fragments and pulp 130 residing in the apex 104 of the trough after the tooth is dissected.

As noted above, most embodiments of the apparatus of the present invention also provide, in the means for advancing the bit 107 toward the trough, a restriction means by which the advance of the bit 107 toward the trough may be controlled, so that the bit does not advance so far as to allow it to crush the pulp and tooth fragments 130 once the tooth is dissected, or crush hard tooth fragments against or into the pulp and tooth fragments and each other 130. However, in the present embodiment of the apparatus of the present invention, a separate means for restricting the movement of the splitting bit 107 is not necessary, as the engagement of the nut 111 with the screw shaft 109 may be finely controlled by relatively small rotational movement of the nut 111.

Figure 8:
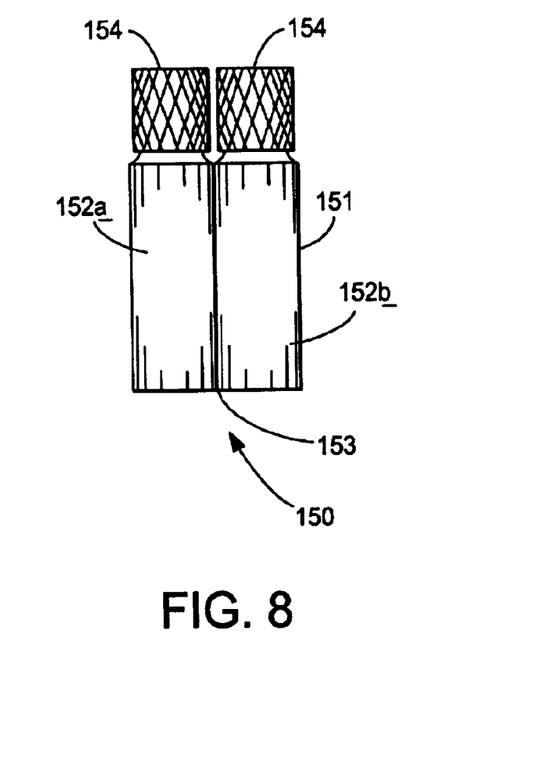
FIG. 8, an exterior view of an exemplary embodiment of the separate collection vessel kit of the present invention, of containing two separate fluids for sterilizing and covering a tooth after extraction or collection in two separate compartments, for housing a tooth or teeth temporarily, or prior to placement of teeth within the dissection vessel of the present invention.

Referring now to FIG. 8, a separate collection vessel kit ("collection kit") is shown. Such a collection kit may be used to temporarily house a tooth prior to its placement within the dissection vessel. An exemplary embodiment of such a collection kit 150 shown in FIG. 8, which kit comprises two tubes having plastic exterior walls 151. The collection kit is capable of containing two separate fluids for covering a tooth after extraction or collection, and may be of any shape, so long the two separate compartments 152a and 152b within the collection kit 150, i.e., the interiors of two tubes in FIG. 8, may be sealed to retain fluids. The two compartments 152a and 152b may be joined or kept separate, however the two compartments are preferably joined, with an impermeable divider wall 153 between. The collection kit has two closure members 154, which may be fit over the two openings (not shown) to the interior of the compartments 152a and 152b to seal them, and thereby retain the fluids within the compartments. The first of the compartments 152a may, and preferably will, have within it a sterilizing medium (not shown), for sterilizing the tooth or teeth extracted or gathered according to the methods of the present invention. The second of the compartments 152b may, and preferably will, have within it, for the protection of the tooth to be dissected, a fluid (not shown), such as the simple saline solution, Ringer's solution, or other isotonic solution found in the dissection vessel of the present invention. The second compartment 152b may also contain EDTA, heparin, or other anti-coagulant.

Figure 7:
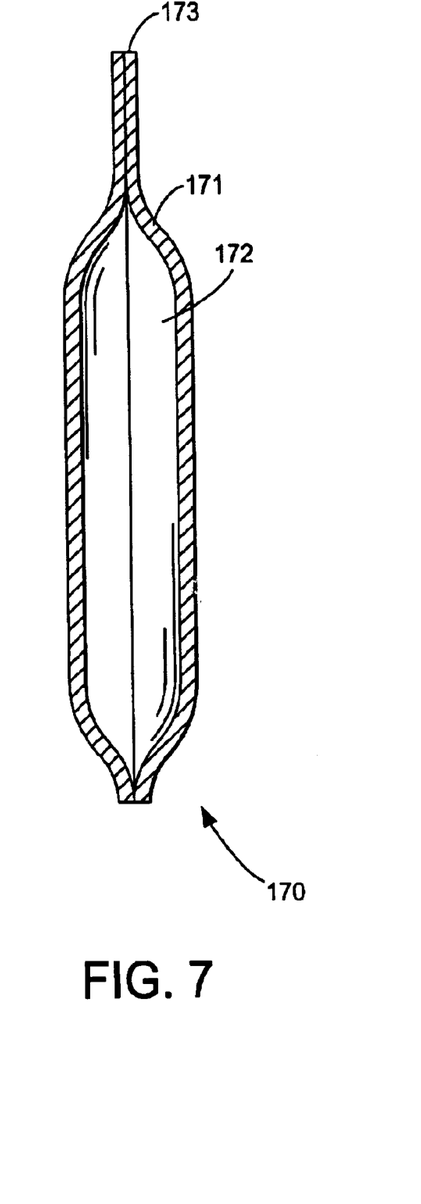
FIG. 7 is a cross sectional diagram of an exemplary embodiment of the shipping container of the present invention, showing an insulative layer, an interior, and an opening formed to allow insertion of the collection kit of the present invention into such interior.
Figure 9:
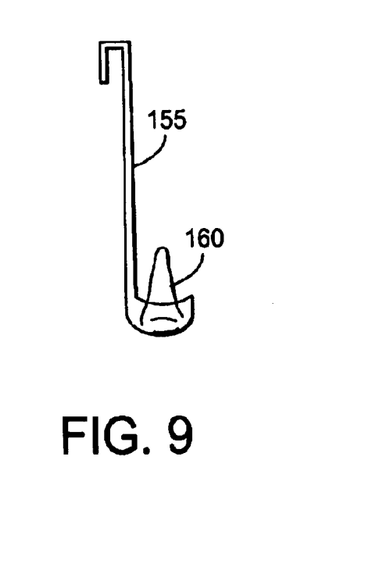
FIG. 9, an exterior view of an exemplary embodiment of the separate ladle of the present invention, which may be utilized in conjunction with the collection vessel kit of the present invention.

Referring to FIG. 9, a separate ladle 155, or other device for handling a tooth or teeth to be dissected 160, may also be provided in the collection kit 150 to reduce the probability of contamination of the tooth after emersion in the sterilization medium. The ladle 155 is preferably stored and shipped within the sterilization compartment 152a. The ladle 155 may be packaged for use in either tube of the collection kit 150, but the ladle 155 is large enough to conveniently hold a large tooth 160, and yet small enough to fit easily through the openings of the compartments 152a and 152b, and into the interiors of such compartments. Referring to FIG. 7, a separate shipping container 170 may also be supplied for ease of transportation to a site for dissection in the event the user is without dissection apparatus such as that of FIG. 4. The shipping container 170 may be formed of insulative material, with an interior 172 sized to snugly fit around the collection kit 150, and closed except for an opening 173 through which the collection kit 150 may fit. Preferably the shipping container 170 bears on its exterior the address of a processing location which may be conveniently reached, and correct postage or messenger account number. The shipping container may also be furnished with a means for cooling the interior 172 (not shown), such as commonly available chemicals which create endothermic reactions upon being stressed. Such chemical might reside in a position immediately surrounding the interior 172, and may be activated just prior to inserting the collection kit 150 within the interior 172 of the shipping container 170.

Utilizing such collection kit 150, with or without the ladle 155 a user may secure a tooth or teeth 160 recently extracted or lost naturally, place the tooth (or teeth) into the sterilizing medium contained within the first compartment 152a of the collection kit immediately after the tooth (or teeth) is extracted or naturally lost, thereby immediately producing, retaining, or reestablishing a sterile field. The user may thereafter place the tooth 160 into the isotonic solution of the second compartment 152b of the collection kit to protect the tooth from the environment for later dissection under controlled conditions. Such transfer is best accomplished utilizing the ladle 155 provided in the collection kit 150. Preferably, the sterilizing medium and isotonic solution are each provided to the user within the compartments 152a and 152b respectively of the collection kit 150, at the time of purchase. However, the sterilizing medium and isotonic solution may also be separately provided in the same collection kit, or separately purchased. Instructions consistent with the methods of the present invention, and consistent with (but not necessarily including all of) the specific steps set forth below, may also be provided in the collection kit 150. Using the collection kit 150, a tooth recently extracted, or gathered by, for example, a mother after natural loss of a tooth by her child, may be treated with sterilizing medium and isotonic solution according to the methods of the present invention. Utilizing the collection kit 150 of FIG. 8 and the ladle of FIG. 9 together, a user may thereby best preserve the fresh pulp found within the tooth against contamination by bacteria, virus and fungi, while also washing the sterilizing medium from the tooth, or diluting it, in the cool neutral isotonic bath. Such storage may be maintained up to the point of dissection, according to the method of the present invention, as depicted most clearly in steps 1 through 3 of FIG. 1, steps 21 through 23 of FIG. 2, and steps 51 through 54 of FIG. 3. More than one tooth may be bathed in sterilizing medium and neutral solution using the collection kit 150. In such case, each such tooth is processed in sterilization medium and isotonic solution for the time required by the methods of the present invention.

The specific steps in utilizing the collection vessel 150 and shipping container 170 comprise: (1) placing the extracted or gathered tooth 160 into ladle 155, (2) unscrewing the closure member 154 of the sterilization compartment 152a, (3) immersing the ladle 155 and tooth 160 into sterilization medium contained in compartment 152a for a time sufficient to sterilize the tooth according to the methods of the present invention, (4) removing the ladle 155 and tooth 160 from the sterilization medium, (5) pour out sterilization medium from compartment 152a or replace and tighten closure member 154, (6) unscrew closure member 154 of the second (neutral) compartment 152b, (7) drop tooth 160 from ladle 155 into the cool isotonic solution within compartment 152b, (8) seal compartment 152b with closure means 154, (9) place collection kit 150 into refrigerator (not freezer), (10) place shipping container 170 into refrigerator, (11) place collection kit 150 within shipping container 170, (12) seal shipping container 170, (13) arrange for messenger pickup of shipping container 170, and deliver into hands of messenger, or deliver shipping container 170 to messenger service location when convenient, (14) transport shipping container by messenger to processing location, and (15) process the tooth by dissecting it, and by taking other steps according to the methods of the present invention. The foregoing steps are equally applicable when two or more teeth are extracted or gathered.

A user may at the time of purchase of a collection kit 150 also be provided with a dissection vessel 100 consistent with the apparatus of the present invention, or other dissection vessel meeting the requirements of the methods of the present invention, as part of an expanded kit. When a dissection vessel and a collection kit are found in the same kit, a tooth recently extracted, or gathered by a mother after natural loss, may then be dissected, and made ready for further processing according to the methods of the present invention after the tooth is treated with sterilizing medium and isotonic solution. A user may thereby best preserve the fresh pulp found within the tooth against contamination by bacteria, virus, and fungi, while also washing the sterilizing medium from the tooth, or diluting it, right up to the time pulp is removed from the tooth.

Figure 11:
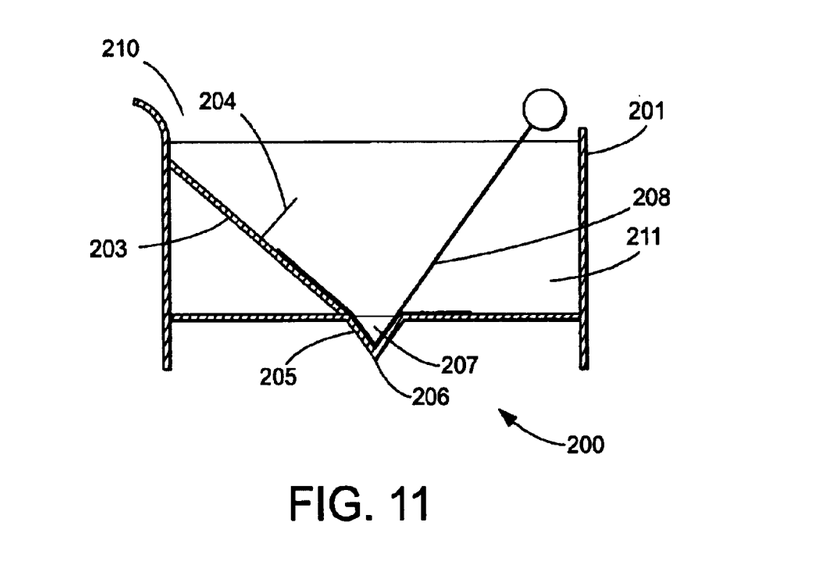
FIG. 11 is a cross sectional diagram of the pulp removal vessel of the present invention, showing the pit in its bottom formed to fit the screen of the collecting assembly of the present invention, the sloped side for directing pulp freed from hard tooth fragments to fall toward the pit.

As noted above, some of the dental pulp from within a tooth may cling to hard tooth fragments after dissection. In such case, a second "pulp removal" vessel, fitted with pulp removal means, is desirable. Referring to FIG. 11, an example of such a separate pulp removal vessel 200 for processing a dissected tooth is shown in cross-section. An exemplary embodiment of such a pulp removal vessel comprises vessel 200 having exterior walls 201, a bottom, an open top 210, and a sharp or barbed projection 204 situated on a sloping side 203 of the pulp removal vessel 200 The pulp removal vessel is capable of containing fluids for covering a tooth during and after dissection, and may be of any shape, so long the vessel 200 retains such fluids during processing within the vessel. The removal vessel 200 has within it a fluid 211, such as simple saline solution, Ringer's solution, or other isotonic solution, for the protection of the tooth to be dissected, and the pulp within the tooth once dissected. As the method of the present invention requires the sterilization of the subject tooth with a sterilizing medium, the fluid 211 within the pulp removal vessel 200 may provide such protection of the tooth by first providing a wash, or dilution of, the sterilization medium. The fluid 211 may also contain anti-coagulant, such as EDTA, heparin, or other anti-coagulant, to retard coagulation during and after the dissection process. The fluid 211 within the pulp removal vessel 200 also assists a tooth placed within the removal vessel to come to rest at a desirable location within the vessel during dissection and removal of pulp from teeth. The removal vessel has an interior sloping side 203, which gathers fragments of pulp and hard tooth fragments as they fall within the fluid 211 or the pulp removal vessel 200 in response to gravity.

Figure 12:
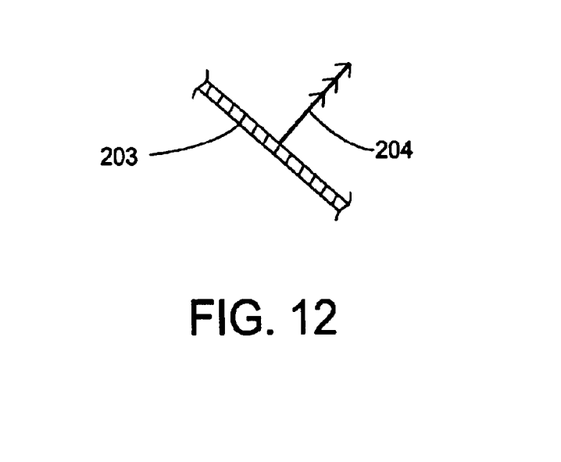
FIG. 12 is a cross sectional diagram of the sharp or barbed projection of the present invention situated on the sloping side of the pulp removal vessel of the present invention, useful for separating tooth fragments and pulp after dissection of a tooth.

Referring to FIG. 12, a convenient arrangement for separating tooth fragments and pulp consist of a sharp or barbed projection 204 situated on the sloping side 203 of the pulp removal vessel 200, upon which the barbed projection 204 a dissected tooth (not shown) may be worked. In so working, the user would present a hard tooth fragment having pulp adhering thereto to the projection 204 so as to catch the pulp on the projection. The user thereafter may pull the hard tooth fragment away from the projection 204, leaving the pulp on the projection, or allowing it to fall off the projection and toward the sloping side 203 of the pulp removal vessel 200. Pulp remaining on the projection 204 may be teased or brushed off, or a separate means (not shown) may be used to disengage the pulp from the projection 204, so that pulp remaining on the projection after working the hard tooth fragment against the projection also may fall off the projection and toward the sloping side 203 of the removal vessel 200. Proceeding from a first tooth fragment to a second tooth fragment, if and as necessary, and so on to other tooth fragments, a user may conveniently pull virtually all pulp from the hard tooth fragments of a tooth or teeth of a donor.

Referring again to FIG. 11, the sloped side 203 of the pulp removal vessel 200 may be sloped sufficiently to allow pulp freed from hard tooth fragments to fall toward a pit 205 in the bottom of the pulp removal vessel 200, the pit having a lowest point at the apex 206 of the pit 205. The pit is formed to receive a screen 207. A collection screen 207, formed to fit within the pit 205, may be attached to a handle 208, thereby creating a pulp collecting assembly 220 for manipulating the screen 207. Once the pulp from a tooth (or teeth) of a donor falls into the pit 205 of the pulp removal vessel, and toward the apex 206 of the pit, the pulp then also falls into the screen 207.

Figure 10:
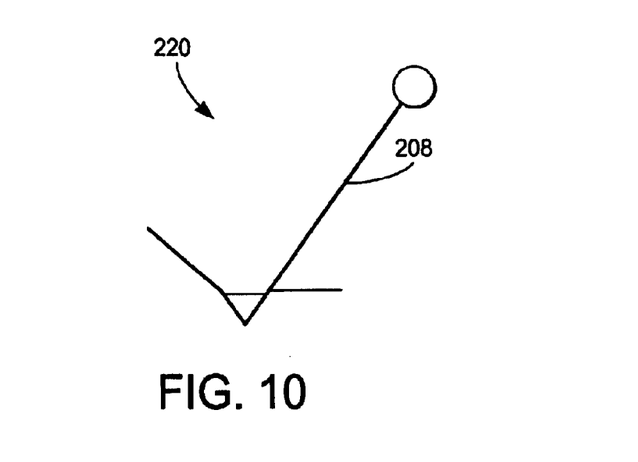
FIG. 10 is a cross sectional diagram of the collecting assembly of the present invention, composed of a collection screen and handle.

Referring again to FIG. 10, the collecting assembly 220 may then be used to transport the pulp to another vial containing anti-coagulant, such as EDTA, heparin, or other anti-coagulant, to retard coagulation, and to mix the pulp with appropriate chemicals for freezing in liquid nitrogen. The pulp may then also be transported to other locations for further manipulation and use using the collecting assembly 220 or other means. By utilizing the apparatus of FIGS. 10, 11 & 12, for pulp removal, the pulp from teeth is impaled on a removal means, such as the sharp or barbed projection 204 situated on a sloping side 203 of the pulp removal vessel 200 of the present invention. The hard pieces of the dissected tooth (not shown), upon which the dental pulp will often adhere, are worked by presenting such tooth fragment to the projection 204 so as to catch the pulp on the projection. The user thereafter proceeds to remove the hard tooth fragment (and other fragments) and the pulp obtained therefrom from the projection 204, and from the pulp removal vessel 200 utilizing the pulp collecting assembly 220. The user then proceeds in the manner set forth above in the general description of the present invention, so that the user obtains virtually all pulp from within a dissected tooth.

Other embodiments of the methods and apparatus of the present invention will be apparent to those skilled in the art by considering the specification and practice of the invention disclosed herein. It is intended that the specification and examples be considered as exemplary only, with the true scope of the invention being indicated by the following claims and equivalents.

What is claimed is:

1. A method for collecting tooth pulp comprising the steps of:
   obtaining a tooth from a donor;
   treating the tooth with sterilizing medium to create a sterile field around the tooth;
   placing the tooth into an isotonic solution containing anti-coagulant; and removing tooth pulp from the tooth.

2. The method for collecting tooth pulp of claim 1, wherein the removing step includes:
   covering the tooth with isotonic solution;
   dissecting the tooth by breaking it into the components of tooth pulp, hard tooth fragments to which no tooth pulp adheres, and hard tooth fragments to which tooth pulp adheres;
   separating tooth pulp from the hard tooth fragments to which tooth pulp adheres; and
   gathering the tooth pulp and separated tooth pulp.

* * * * *